United States Patent [19]
Fowler

[11] Patent Number: 6,042,813
[45] Date of Patent: Mar. 28, 2000

[54] SUNSCREEN HAVING DISAPPEARING COLOR INDICATOR

[75] Inventor: Kevin C. Fowler, Millington, Tenn.

[73] Assignee: Schering-Plough HealthCare Products, Inc., Memphis, Tenn.

[21] Appl. No.: 09/303,414

[22] Filed: May 3, 1999

Related U.S. Application Data

[60] Provisional application No. 60/084,180, May 4, 1998.

[51] Int. Cl.⁷ .............................. A61K 7/42; A61K 7/44; A61K 7/00
[52] U.S. Cl. ............................. 424/59; 424/60; 424/400; 424/401
[58] Field of Search ................................ 424/59, 60, 400, 424/401

[56] References Cited

U.S. PATENT DOCUMENTS

| | | | |
|---|---|---|---|
| 5,523,075 | 6/1996 | Fuerst et al. | 424/59 |
| 5,567,420 | 10/1996 | McEleney et al. | 424/60 |
| 5,747,011 | 5/1998 | Ross et al. | 424/59 |

FOREIGN PATENT DOCUMENTS

| | | | |
|---|---|---|---|
| 94/26233 | 11/1994 | WIPO | A61K 7/00 |

OTHER PUBLICATIONS

Fishman, "Certified Dyes", Happi, p. 28, Jan. 1995.
"Concise Encyclopedia Chemistry", Walter de Gruyter, Berlin, New York, pp. 437 and 438, 1994.

*Primary Examiner*—Shelley A. Dodson
*Attorney, Agent, or Firm*—Robert A. Franks

[57] ABSTRACT

A colored sunscreen emulsion which enables the user to more effectively protect against skin damage, by facilitating more complete and uniform coverage of the sunscreen on the skin, comprises:

a) at least one oil-soluble dye that imparts a color other than white to the sunscreen, in amounts such that when the emulsion is rubbed into the skin, the color substantially disappears;

b) at least one sunscreen active agent in an amount effective to protect skin against the actinic radiation of the sun;

c) at least one emulsifier;

d) sufficient water to form the colored emulsion; and e) optionally, one or more ingredients from one or more of the following classes: emollients, humectants, dry-feel agents, waterproofing agents, preservatives, antioxidants, chelating agents, insect repellents and fragrances.

21 Claims, No Drawings

SUNSCREEN HAVING DISAPPEARING COLOR INDICATOR

CROSS-REFERENCE TO RELATED APPLICATION

This application claims benefits under 35 U.S.C. § 119(e) from provisional application No. 60/084,180 filed on May 4, 1998.

INTRODUCTION TO THE INVENTION

The invention relates to compositions for skin application, to protect against the effects of ultraviolet radiation exposure.

Sunscreens are substances or compositions applied to the skin to protect the skin from damage, such as sunburn, due to excessive exposure to ultraviolet radiation. The typical commercial product is an emulsion, preferably an emulsion having a continuous (external) aqueous phase and a discontinuous (internal) oily phase; such "oil-in-water" emulsions have a particularly pleasing feel when applied to the skin, since the sensation is one of applying an aqueous material. Most of such products are sold in the form of lotions. When uniformly applied to the body, sunscreens can be highly effective in protecting against damage. However, less effective protection can occur when areas of the body are unevenly covered because the sunscreen is hard to see while being spread onto the skin. Children may be at greater risk of damage than adults, since self-applied coverage on children's skin tends to be more incomplete, uneven or inconsistent, and children tend to be less aware of their sunburn condition until it becomes serious.

PCT International Patent Application WO 94/26233 teaches that phenolphthalein, an acid-base indicator, can be added to sunscreens to create a disappearing pink coloration, provided the sunscreens are formulated at a pH greater than 9.0. However, phenolphthalein can induce skin rashes and eruptions. Additionally, formulations with this pH are too highly alkaline and can be irritating to the skin.

PCT International Patent Application WO 95/28912 teaches composite UV sunblock compositions that may contain colored particles. However, when the sunscreen of WO 95/28912 is topically applied to the skin, the sunscreen remains visibly colored.

U.S. Pat. No. 5,747,011 relates to a colored sunscreen composition which "disappears" when dried on the skin or rubbed into the skin. The composition incorporates water-soluble dyes, as the color formers. However, it has been discovered that some common fabrics can be indelibly stained by at least some of the dyes, when the composition contacts the fabrics.

Accordingly, an approach was sought to provide a colored sunscreen formulation which could be readily visualized while the sunscreen is being applied to the skin, but would substantially disappear when rubbed into the skin, and which has a reduced potential for fabric staining.

SUMMARY OF INVENTION

It has been surprisingly and unexpectedly found that although the inclusion of an oil-soluble dye to a sunscreen emulsion can render the sunscreen visually colored, that such coloration will substantially disappear when the sunscreen emulsion is rubbed into the skin.

Thus, in one embodiment, the present invention is directed toward a colored sunscreen emulsion comprising:

a) at least one oil-soluble dye that imparts a color other than white to the sunscreen emulsion, in amounts such that when the sunscreen emulsion is rubbed into the skin, the color substantially disappears;

b) at least one sunscreen active in an amount effective to protect against the actinic radiation of the sun;

c) at least one emulsifier; and d) sufficient water to form the colored emulsion.

The amount of the oil-soluble dye in the emulsion can range from about 0.0005 to about 0.5 weight percent of the emulsion, preferably from about 0.002 to about 0.2 weight percent of the emulsion. Also preferred is that the emulsion is an oil-in-water emulsion.

Optionally, the colored, sunscreen emulsion can contain one or more additional ingredients, including emollients, waterproofing agents, dry-feel modifiers, antimicrobial preservatives, insect repellents and/or fragrances.

In another embodiment, the present invention is directed towards a method for protecting the skin against sunburn comprising topically applying the sunscreen emulsion as described above to the skin.

An advantage of the present invention is that it provides a sunscreen and a method for protecting against sunburn that enables the user to apply the sunscreen more completely and uniformly to the skin, thus providing more effective protection against sunburn.

A second advantage of the present invention is that it provides a sunscreen with a color indicator which has a low potential for indelibly staining fabrics, when promptly cleaned therefrom.

A third advantage of the present invention is that it provides a colored sunscreen and a method for protecting against sunburn which is more enjoyable for children to use because of the attractiveness and appealing nature of the color indicator.

DETAILED DESCRIPTION OF THE INVENTION

In the present specification, the terms "emulsion," "formulation" and "composition" can be used interchangeably. The emulsion of the present invention contains one or more oil-soluble dyes, one or more sunscreen actives, one or more emulsifiers, water; and may optionally contain one or more emollients, humectants, dry-feel agents, waterproofing agents, preservatives, antioxidants, chelating agents, insect repellents and fragrances.

Oil-Soluble Dyes

Certified dyes are synthetic organic substances which are manufactured so that each batch passes a U.S. Food & Drug Administration (FDA) purity inspection. If approved by the FDA, these dyes are certified for use in foods, drugs, cosmetics (FD&C colors), drugs and cosmetics only (D&C colors), or only in topically applied drugs and cosmetics (external D&C colors).

Oil-soluble, certified dyes are used mostly in water resistant cosmetic products, including foundations and eye liners. Among the certified dyes which are useful in the present invention are those denoted D&C Green #6, D&C Violet #2, D&C Red #17 and D&C Yellow #11. The adopted names for the foregoing dyes, when not certified according to FDA regulations, are respectively: solvent green 3; solvent violet 13; solvent red 23; and solvent yellow 33. The noncertified versions of the dyes are also useful in the invention, where their use is legally permitted.

It is desirable to use dyes which form colors easily visualized when a sunscreen-effective amount of the formulation is spread onto the skin. The more preferred colors include blue, purple, violet, yellow, green and aqua, all of which colors contrast with the skin quite vividly. Many appropriate colors can be produced by mixing two or more of the readily available dyes, in desired proportions.

The sunscreen emulsion should contain the oil-soluble dye in an amount sufficient to enable the sunscreen to be readily visualized when initially applied to the skin, but in which the color substantially disappears when the sunscreen emulsion is rubbed into the skin. One or more oil-soluble dyes can be employed in the composition, in an amount totaling about 0.0005 to about 0.5% by weight of the sunscreen composition, preferably from about 0.002 to about 0.2%, and more preferably from about 0.01 to about 0.1%

Since the dyes are oil-soluble, they will be a part of the internal phase of an oil-in-water or water-in-oil-in-water emulsion, and therefore will be less available to stain fabrics with which the emulsion may come in contact. Unless the emulsion is allowed to de-emulsify, such as by drying, a simple rinse or treatment with a soap solution can remove at least most of the staining potential before the dye is incorporated into the fibers.

Sunscreen Active Ingredients

The compositions of the present invention can contain a sunscreening effective amount of one or more oil-soluble or water-soluble sunscreening UV-B active agents or a mixture of one or more UV-B actives and one or more UV-A actives. UV-A type sunscreening actives protect against longer-wavelength actinic radiation of the sun in the 320 to 400 nm range and UV-B type sunscreening actives protect against shorter wavelength actinic radiation of the sun in the 290–320 nm range.

Typical sunscreen actives include: aminobenzoic acid at up to about 15 weight percent; cinoxate at up to about 3 weight percent; avobenzone at up to about 3 weight percent or about 2 to 3% in admixture with one or more other sunscreen active agents; diethanolamine methoxycinnamate at up to about 10 weight percent or about 8 to 10% in admixture; digalloyl trioleate at up to about 5 weight percent or about 2 to 5% in admixture; dioxybenzone at up to about 3 weight percent alone or in admixture; ethyl 4-[bis(hydroxypropyl)]-aminobenzoate at up to about 5 weight percent or about 1 to 5% in admixture; glyceryl aminobenzoate at up to about 3 weight percent or about 2 to 3% in admixture; homosalate at up to about 15 weight percent or about 4 to 15% in admixture; lawsone at up to about 0.25 weight percent, together with dihydroxyacetone at up to about 3 weight percent, alone or in admixture; menthyl anthranilate at up to about 5 weight percent or about 3.5 to 5% in admixture; octocrylene at up to about 10 weight percent or 7 to about 10% in admixture; octyl methoxycinnamate at up to about 7.5 weight percent or about 2 to 7.5% in admixture; octyl salicylate at up to about 5 weight percent or about 3 to 5% in admixture; oxybenzone (benzophenone-3) at up to about 6 weight percent or about 2 to 6% in admixture; padimate O at up to about 8 weight percent or about 1.4 to 8% in admixture; phenylbenzimidazole sulfonic acid at up to about 4 weight percent or about 1 to about 4% in admixture; red veterinary petrolatum at up to about 100 percent or at least about 30% in admixture; sulisobenzone at up to about 10 weight percent or about 5 to 10% in admixture; titanium dioxide at up to about 25 weight percent or about 2 to 25% in admixture; and trolamine salicylate at up to about 12 weight percent or about 5 to 12% in admixture.

Typical suitable UV-B type sunscreening actives include benzophenone-3, benzophenone-8, substituted para-aminobenzoates, alkyl esters of para-methoxycinnamate such as octyl p-methoxycinnamate, available from Givaudan Corp., Clifton, N.J. U.S.A. under the tradename Parsol MCX, and octyl salicylate available from Harmann and Riemer, Springfield, N.J. U.S.A. The amount of UV-B type sunscreening active should be sufficient to give an SPF of 2 to at least 15.

Typical suitable UV-A type sunscreening actives include oxybenzone and avobenzone. Sunscreen emulsions containing mixtures of UV-B and UV-A type sunscreen actives should be able to provide an SPF of 2 to at least 50.

Except as noted otherwise, one or more sunscreen actives can be employed in the composition in amounts up to about 35 weight percent, preferably about 12 to about 30 weight percent of the sunscreen composition, more preferably from about 5 to about 20 weight percent.

Emulsions/Emulsifiers

A stable emulsion is a mixture of two immiscible liquids, i.e. liquids that are not mutually soluble, but which can form a fluid in which very small droplets of one component are stably dispersed throughout the other liquid, giving the mixture the appearance of a homogeneous fluid. Emulsions can include particulate materials and materials which are solid or solid-like at room temperature, but which will liquefy at higher temperatures used during formation of the emulsion. The presence of an emulsifier enhances the ability of one of the immiscible liquids to remain in a continuous form, while allowing the other immiscible liquid to remain in a dispersed droplet form. Thus, one function of an emulsifier, a stabilizing compound, is to assist in the production of a stable emulsion. A secondary function of emulsifiers is to provide a thickening or "bodying" to an emulsion. Typically, emulsifiers are molecules with non-polar and polar parts that are able to reside at the interface of the two immiscible liquids. As used herein in reference to the emulsifiers, the term "HLB value" means the hydrophilic/lipophilic balance. The HLB value has been used by those skilled in the emulsion art as an approximate (but certainly not infallible) guide to selecting specific emulsifiers useful for preparing the various types of emulsions. In general, the higher HLB (i.e., over about 7) values predict usefulness of an emulsifier for producing oil-in-water emulsions.

An oil-in-water (o/w) emulsion is a mixture where water-insoluble droplets (the discontinuous phase) are dispersed in a continuous aqueous phase. A water-in-oil (w/o) emulsion is a mixture where water droplets (the discontinuous phase) are dispersed in a continuous oily phase. Preferably the composition of the present invention is an oil-in-water emulsion where the oil-soluble actives are dispersed in the oil phase, prior to mixture with the water phase. The type of emulsion, oil-in-water (o/w) or water-in-oil (w/o), formed is sometimes determined by the volume ratio of the two liquids, provided the ratio is sufficiently high. For example, with 95% water and 5% oil phases (an o/w phase ratio of 19), the emulsion likely will become o/w. For moderate ratios (<3), the type of emulsion is decided by several factors, such as order of addition or type of emulsifier. One liquid slowly added to a second liquid with vigorous agitation usually results in the second liquid being the continuous phase. Another factor is preferred solubility of the emulsifier, the phase in which the emulsifier is soluble most probably is continuous.

More complex emulsions such as double emulsions are formed where an emulsion is dispersed in a continuous phase. For example, in an oil in-water-in oil (o/w/o) emulsion, the water in a continuous water phase containing dispersed oil droplets is itself dispersed in a continuous oil phase. Similarly, in a water-in oil-in water (w/o/w) emulsion, the oil in a continuous phase containing dispersed water droplets is itself dispersed in a continuous water phase. These more complex emulsions, however, are not commonly used for products such as sunscreens.

Emulsifiers useful in the present invention may be anionic, cationic or non-ionic, and either liquid or solid at room temperature. Emulsifiers which are salts may be formed in-situ when their constituents (such as stearic acid and triethanolamine, which form TEA-stearate) are present together in the formulation. Suitable emulsifiers include, without limitation, sorbitan esters such as sorbitan isostearate available as Crill 6, tradename of Croda Inc. of New York, N. Y. U.S.A.; polyglyceryl-3 distearate available as Cremophor GS-32, tradename of BASF, Parsippany, N.J. U.S.A.; carbomer, which is a homopolymer of acrylic acid crosslinked with an allyl ether of sucrose, available as Carbopol 941, tradename of B.F. Goodrich, Cleveland, Ohio U.S.A. Other useful emulsifiers include ceteareth-15, cetyl alcohol, cetyl phosphate, dimethicone copolyol phosphate, glyceryl isostearate, hydrogenated lecithin, laureth-12, PEG-20 distearate, PEG-8 oleate, PEG-40 sorbitan diisostearate, polyglyceryl-10 distearate, polysorbate 20, polysorbate 80, PPG-7 lauryl ether, sodium laureth sulfate, sorbitan sesquioleate and acrylates/$C_{10-30}$ alkyl acrylate crosspolymer; these are only representatives from some of the useful emulsifier chemical classes.

During preparation of the emulsion, an acid or a base may be added to adjust the pH of one or more ingredients, e.g. to adjust the viscosity of a polymeric thickener, prior to its inclusion in the sunscreen composition. For example, triethanolamine, a base, can be used to increase the pH of the water phase and consequently modify the desired viscosity of the emulsion. The sunscreen typically has a pH of about 4 to about 9, preferably from about 6.5 to about 8.5; more preferably the pH of the sunscreen is approximately neutral, i.e. about 7.

Conveniently, one or more emulsifiers can be used in the compositions of the present invention in amounts ranging from about 0.05 to about 20 weight percent of emulsion, preferably from about 0.1 to about 15 percent, more preferably from about 5 to about 10 percent.

Water

Water is employed in amounts effective to form the emulsion. It is preferred to use water which has been subjected to purification procedures such as deionization or reverse osmosis, to minimize formulation inconsistencies due to dissolved solids in the water. The amount of water in the emulsion or composition can range from about 2 to 95 weight percent, preferably from 40 to 85 percent.

Emollients

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil.

Other suitable emollients include, without limitation, squalane, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate which is commercially available as Lexol EHP, tradename of Inolex Co. of Philadelphia, Pa. U.S.A., isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricinoleates and esters of alcohols and polyalcohols such as isopropyl adipate, hexyl laurate and octyl dodecanoate.

Other suitable emollients which are solids or semi-solids at ambient temperatures may be used. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the sunscreen emulsion in an amount ranging from about 10 to about 50 weight percent, preferably about 20 to about 40 percent.

Humectants

A humectant is a moistening agent that promotes retention of water due to its hygroscopic properties. Suitable humectants include glycerin, polymeric glycols such as polyethylene glycol and polypropylene glycol, mannitol and sorbitol. One or more humectants can optionally be included in the in the sunscreen in amounts from about 1 to 10 weight percent.

Dry-Feel Modifier

A dry-feel modifier is an agent which when added to a emulsion, imparts a "dry feel" to the skin when the emulsion dries. Dry-feel modifiers may also reduce sunscreen migration on the skin. Dry feel modifiers can include starches, talc, kaolin, chalk, zinc oxide, silicone fluids, inorganic salts such as barium sulfate and sodium chloride, $C_6$ to $C_{12}$ alcohols such as octanol; sulfonated oils; surface treated silica, precipitated silica, fumed silica such as Aerosil® available from the Degussa Inc. of New York, N.Y. U.S.A. or mixtures thereof; dimethicone, a mixture of mixture of methylated linear siloxane polymers, available as DC200 fluid, tradename of Dow Corning, Midland, Mich. U.S.A. One or more dry-feel modifiers can optionally be included in the sunscreen in amounts ranging from 0.01 to about 20 weight percent, preferably from about 0.5 to about 6 weight percent.

Waterproofing Agents

A waterproofing agent is a hydrophobic material that imparts film forming and waterproofing characteristics to an emulsion. Typical suitable waterproofing agents include copolymers derived from polymerization of octadecene-1 and maleic anhydride in accordance with the procedures in U.S. Pat. No. 3,860,700 and Re. 28,475. A preferred waterproofing agent is a polyanhydride resin, also known as PA-18, tradename of the Chevron Chemicals Co., San Francisco, Calif. U.S.A. Another preferred waterproofing agent is a copolymer of vinyl pyrollidone and eicosene monomers such as Ganex Polymer, tradename of ISP Inc. of Wayne, N.J. U.S.A.

The waterproofing agent is preferably used in amounts effective to maintain the sunscreen effectiveness on the skin following exposure to circulating water for at least 80 minutes, using the procedures described by the U.S. Food and Drug Administration in "Sunscreen Drug Products for OTC Human Use," Federal Register, Vol. 43, Aug. 25, 1978, Part 2, pp. 38206–38269. One or more waterproofing agents can optionally be included in the sunscreen composition in an amount ranging from about 0.01 to about 10 weight percent, preferably about 1 to about 10 percent.

Antimicrobial Preservative

An antimicrobial preservative is a substance or preparation which destroys, or prevents or inhibits the proliferation of, microorganisms in the sunscreen composition, and which may also offer protection from oxidation. Preservatives are frequently used to make self-sterilizing, aqueous based products such as emulsions. This is done to prevent the development of microorganisms that may be in the product from growing during manufacturing and distribution of the product and during use by consumers, who may further inadvertently contaminate the products during normal use. Among the numerous typical preservatives are the lower alkyl esters of para-hydroxybenzoates (parabens) especially, methylparaben, propylparaben, isobutylparaben and mixtures thereof, imidazolidinyl urea, benzyl alcohol and benzoic acid. One or more antimicrobial preservatives can optionally be included in the sunscreen composition in an amount ranging from about 0.001 to about 10 weight percent, preferably about 0.05 to about 2 percent.

Antioxidants

An antioxidant is a natural or synthetic substance added to the formulation to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, vitamin E, vitamin E acetate, vitamin C and alkylated parabens such as methylparaben and propylparaben. One or more antioxidants can optionally be included in the sunscreen composition in an amount ranging from about 0.001 to about 5 weight percent, preferably about 0.05 to about 2 percent.

Chelating Agents

Chelating agents are substances used to chelate or bind metallic ions, such as with a certain heterocyclic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.1 weight percent.

Fragrances

Fragrances are aromatic substances which can impart an aesthetically pleasing aroma to the sunscreen composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the sunscreen composition in an amount ranging from about 0.001 to about 10 weight percent, preferably about 0.05 to about 5 percent.

Insect Repellents

Insect repelling components are desirable in sunscreening emulsions, since the emulsions are normally used primarily by persons engaged in outdoor activities. The most widely used active agent for personal care products is N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

Dispensers

The sunscreen emulsions of the present invention containing the disappearing color indicator can be stored or dispensed in any container suitable for convenient delivery, i.e. pouring or spraying. Such containers can include but are not limited to jars, bottles, lotion pump bottles, pump spray bottles and pressurized aerosols.

Application Method

To achieve the maximum possible uniformity of application to the skin, the sunscreen lotions of the invention should be spread onto exposed skin in sufficient amounts to yield a distinctly visible uniform layer of colored lotion. After it is visually verified that the desired coverage has been obtained, the lotion should be rubbed into the skin to cause the visible color to disappear. As with most sunscreen products, it is recommended that the sunscreen be applied shortly (e.g., 15 minutes) prior to commencing exposure to ultraviolet radiation; this permits the emulsion to break apart, due to evaporation of its contained water, and frees the active ingredients from the formulation.

The visualization and disappearance of the sunscreen on the skin can be evaluated using visual, chromatographic and pantone matching systems.

To evaluate the color indicator on the skin, it is helpful to have an objective, instrumental measurement of colors and intensities. Accordingly, a method has been developed using the Minolta Chroma Meter Model CR-200, which uses reflected light from a surface and gives results in terms of the CIE (International Commission on Illumination) tristimulus values. These values are subsequently transformed mathematically into the L* a* b* color space, wherein the magnitudes of changes in hue and intensity of color correspond closely with those perceived by the human eye.

L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y axis, to give quantitative color information: "metric chroma" is the length of a line from the origin (a*=0b , b*=0) to the point of a sample reading, while "metric hue angle" is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The meter can be used to measure a base line skin tone as well as residual color left on the skin after "rub out" with a number of subjects, to establish a target for disappearance of color applied to the skin.

Definitions and suppliers of many of the ingredients mentioned above or used in the following illustrative examples may be found in J. M. Nikitakis et al., Eds., *CTFA International Cosmetic Ingredient Dictionary, Fourth Ed.*, The Cosmetic, Toiletry and Fragrance Association, 1101 17th Street NW, Washington, D.C. 20036 U.S.A., 1991. This dictionary lists the chemical and adopted names, and commercial designations, of many of the substances mentioned herein.

The following examples are provided solely to further illustrate the invention, and are not intended to limit the scope of the invention as it is defined by the appended claims. Percentages given throughout this specification and claims indicate, unless the context clearly dictates otherwise, percent by weight.

EXAMPLE 1

A kilogram batch of sunscreen lotion, having an SPF value of 30 and a violet color, is prepared according to the invention using the following components:

| Component | Grams |
|---|---|
| Part A | |
| Stearic acid, NF | 20 |
| Sorbitan isostearate | 40 |
| Octyl p-methoxycinnamate | 75 |
| Homomenthyl salicylate | 80 |
| Benzophenone-3 | 60 |
| Octyl salicylate | 15 |
| Jojoba oil | 0.5 |
| Aloe vera lipoquinone | 0.5 |
| Propylparaben | 1 |
| Polyglyceryl-3 distearate | 30 |
| D & C Violet #2 | 0.5 |
| Part B | |
| Octadecene/maleic anhydride copolymer | 30 |
| Dimethicone | 4 |
| Vitamin E acetate | 1 |
| Part C | |
| Octyl salicylate | 35 |
| Barium sulfate | 17.5 |
| Part D | |
| Water | 190 |
| Carbomer 941 | 0.25 |
| Part E | |
| Water | 247.15 |
| Sorbitol 70% aqueous solution | 50 |
| Triethanolamine | 22.5 |
| Methylparaben | 2 |
| Disodium EDTA | 0.1 |
| Part F | |
| Benzyl alcohol | 10 |
| Fragrance | 6 |
| Part G | |
| Water | 62 |

The following procedure is used to prepare the lotion: (1) combine the Part A components and, with stirring, heat the mixture to about 82–85° C., then add the octadecene/maleic acid copolymer from Part B and stir to dissolve; (2) cool the step 1 mixture to about 77–79° C. and add the remaining Part B components with continuous mixing; (3) in another vessel, sprinkle the barium sulfate onto the well agitated octyl salicylate of Part C, mix for 30 minutes and then combine this dispersion with the mixture of step 2; (4) in a vessel sized to contain the entire production batch, combine the Part D components and mix to form a smooth, lump-free mixture; (5) sequentially add the components of Part E to the step 4 mixture, reserving the triethanolamine, heat to about 77–82° C. with continuous mixing, then add the triethanolamine when a clear solution is achieved; (6) add the Part G component to the solution of step 5, with mixing; (7) add the oil phase from step 3 to the aqueous phase from step 6 with vigorous mixing, then, with normal mixing, begin cooling the formed emulsion to ambient temperature; and (8) as the temperature falls through about 49° C. add the Part F components and sufficient water to compensate for any evaporative losses which occurred during the procedure.

The violet lotion is highly visible as it is being spread onto the skin, but substantially disappears as the formulation is rubbed into the skin.

EXAMPLE 2

A kilogram batch of sunscreen lotion, having an SPF value of 30 and a green color, is prepared according to the invention using the following components and the procedure of the preceding example:

| Component | Grams |
|---|---|
| Part A | |
| Stearic acid, NF | 20 |
| Sorbitan isostearate | 40 |
| Octyl p-methoxycinnamate | 75 |
| Homomenthyl salicylate | 80 |
| Benzophenone-3 | 60 |
| Octyl salicylate | 15 |
| Jojoba oil | 0.5 |
| Aloe vera lipoquinone | 0.5 |
| Propylparaben | 1 |
| Polyglyceryl-3 distearate | 30 |
| D & C Green #6 | 1 |
| Part B | |
| Octadecene/maleic anhydride copolymer | 30 |
| Dimethicone | 4 |
| Vitamin E acetate | 1 |
| Part C | |
| Octyl salicylate | 35 |
| Barium sulfate | 17.5 |
| Part D | |
| Water | 190 |
| Carbomer 941 | 0.25 |
| Part E | |
| Water | 246.65 |
| Sorbitol, 70% aqueous solution | 50 |
| Triethanolamine | 22.5 |
| Methylparaben | 2 |
| Disodium EDTA | 0.1 |
| Part F | |
| Benzyl alcohol | 10 |
| Fragrance | 6 |
| Part G | |
| Water | 62 |

The green lotion is highly visible as it is being spread onto the skin, but substantially disappears as the formulation is rubbed into the skin.

What is claimed is:

1. A colored sunscreen emulsion comprising:

a) at least one oil-soluble dye that imparts a color other than white to the sunscreen emulsion, to render the emulsion highly visible while it is being spread onto the skin, but which color substantially disappears when the spread emulsion is rubbed into the skin;

b) at least one sunscreen active agent in an amount effective to protect skin against the actinic radiation of the sun;

c) at least one emulsifier; and d) sufficient water to form the colored emulsion.

2. The colored sunscreen emulsion of claim 1, wherein the dye is a D&C color or a noncertified equivalent thereof, or a mixture of two or more D&C colors or noncertified equivalents.

3. The colored sunscreen emulsion of claim 1, wherein the dye imparts a blue, purple, violet, yellow, green or aqua color to the sunscreen emulsion.

4. The colored sunscreen of claim 1, wherein the dye comprises one or more members selected from the group consisting of D&C Violet #2, D&C Green #6, D&C Yellow #11, D&C Red #17 and noncertified equivalents thereof.

5. The colored sunscreen emulsion of claim 1, wherein the dye comprises D&C Violet #2 or a noncertified equivalent thereof.

6. The colored sunscreen emulsion of claim 1, wherein the dye comprises D&C Green #6 or a noncertified equivalent thereof.

7. The colored sunscreen emulsion of claim 1, wherein the amount of the dye ranges from about 0.0005 to about 0.5 weight percent of the emulsion.

8. The colored sunscreen emulsion of claim 1, wherein the amount of the dye ranges from about 0.002 to about 0.2 weight percent of the emulsion.

9. The colored sunscreen emulsion of claim 1, wherein the amount of the dye ranges from about 0.01 to about 0.1 weight percent of the emulsion.

10. The colored sunscreen emulsion of claim 1, which is an oil-in-water emulsion (o/w).

11. The colored sunscreen emulsion of claim 1, which is a water-in-oil-in water emulsion (w/o/w).

12. The colored sunscreen emulsion of claim 1 having a pH about 4 to about 9.

13. The colored sunscreen emulsion of claim 1 having a pH about 6.5 to about 7.5.

14. The colored sunscreen emulsion of claim 1, further comprising one or more emollients.

15. The colored sunscreen emulsion of claim 1, further comprising one or more waterproofing agents.

16. The colored sunscreen emulsion of claim 1, further comprising one or more antimicrobial preservatives.

17. The colored sunscreen emulsion of claim 1, further comprising one or more dry-feel modifiers.

18. The colored sunscreen emulsion of claim 1, further comprising one or more fragrances.

19. The colored sunscreen emulsion of claim 1, further comprising one or more insect repellents.

20. A method for protecting the skin against damage from exposure to ultraviolet radiation, comprising topically applying to the skin the colored sunscreen emulsion of claim 1.

21. A colored sunscreen emulsion comprising:

a) about 0.0005 to about 0.5 weight percent of at least one oil-soluble dye selected from the group consisting of D&C Violet #2, D&C Green #6, D&C Yellow #11, D&C Red #17, noncertified equivalents thereof and mixtures of any two or more of the foregoing, in an amount sufficient to impart a color other than white to the sunscreen emulsion to render the emulsion highly visible while it is being spread onto the skin, but which color substantially disappears when the spread emulsion is rubbed into the skin;

b) at least one sunscreen active agent in an amount effective to protect skin against the actinic radiation of the sun;

c) at least one emulsifier; and d) sufficient water to form the colored emulsion.

* * * * *